US012721517B2

(12) United States Patent
Lagorce et al.

(10) Patent No.: US 12,721,517 B2
(45) Date of Patent: Sep. 1, 2026

(54) PUPIL DETECTION USING AN EVENT-BASED SENSOR

(71) Applicant: PROPHESEE, Paris (FR)

(72) Inventors: Xavier Lagorce, Saint-Maur-des-Fossés (FR); Germain Haessig, Vienna (AT); Damien Joubert, Rouen (FR); Thomas Finateu, Veneux les sablons (FR)

(73) Assignee: PROPHESEE, Paris (FR)

(*) Notice: Subject to any disclaimer, the term of this patent is extended or adjusted under 35 U.S.C. 154(b) by 44 days.

(21) Appl. No.: 18/659,954

(22) Filed: May 9, 2024

(65) Prior Publication Data

US 2024/0374133 A1 Nov. 14, 2024

(30) Foreign Application Priority Data

May 9, 2023 (EP) .................................... 23315173

(51) Int. Cl.
*A61B 3/113* (2006.01)
*G02B 27/00* (2006.01)
*G06F 3/01* (2006.01)

(52) U.S. Cl.
CPC .......... *A61B 3/113* (2013.01); *G02B 27/0093* (2013.01); *G06F 3/013* (2013.01)

(58) Field of Classification Search
CPC ..... A61B 3/113; G02B 27/0093; G06F 3/013; G06F 3/005; G06V 10/147; G06V 40/19; G06V 10/141; G06V 10/143; G06V 40/18; G06V 10/62; G06V 40/193
See application file for complete search history.

(56) References Cited

U.S. PATENT DOCUMENTS

| | | | | |
|---|---|---|---|---|
| 7,506,011 | B2 * | 3/2009 | Liu | G06F 16/273 |
| 8,305,899 | B2 * | 11/2012 | Luo | H04W 8/04 370/428 |
| 11,543,883 | B2 | 1/2023 | Boyle et al. | |
| 2012/0237461 | A1 * | 9/2012 | Yu | A61K 8/25 424/59 |
| 2012/0251600 | A1 * | 10/2012 | Yu | A61K 8/585 424/78.03 |
| 2014/0004073 | A1 * | 1/2014 | Yu | A61Q 19/08 424/78.03 |
| 2015/0323525 | A1 * | 11/2015 | Vidarsson | G01N 33/54373 506/9 |
| 2016/0116740 | A1 * | 4/2016 | Takahashi | G02B 27/017 345/8 |
| 2017/0100032 | A1 * | 4/2017 | Zakariaie | A61B 3/0025 |
| 2017/0150133 | A1 * | 5/2017 | Yoshida | H04N 13/393 |

OTHER PUBLICATIONS

Extended European Search Report in European Patent Application No. 23315173.7, Sep. 22, 2023, 7 pages.

* cited by examiner

*Primary Examiner* — Frank F Huang

(57) ABSTRACT

A method for detecting a pupil of an eye with an event-based vision sensor, comprises the steps of directing a first light source towards the eye; observing the eye with the event-based vision sensor; and intermittently submitting the event-based vision sensor to a uniform background signal.

11 Claims, 2 Drawing Sheets

Eye

Pupil
14
10

12
14
10
16
12

Amplitude (lin)
Eye
Pupil

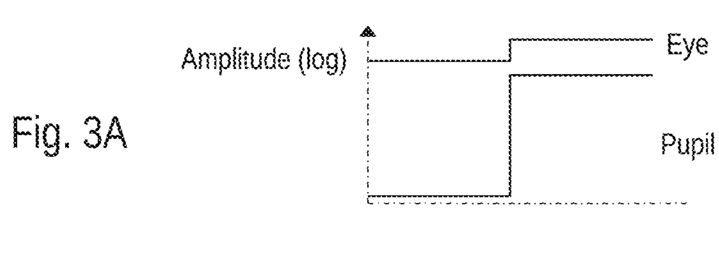
Fig. 3A
Amplitude (log)
Eye
Pupil
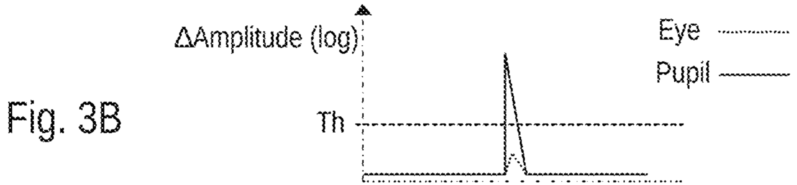
Fig. 3B
ΔAmplitude (log)
Eye
Pupil
Th
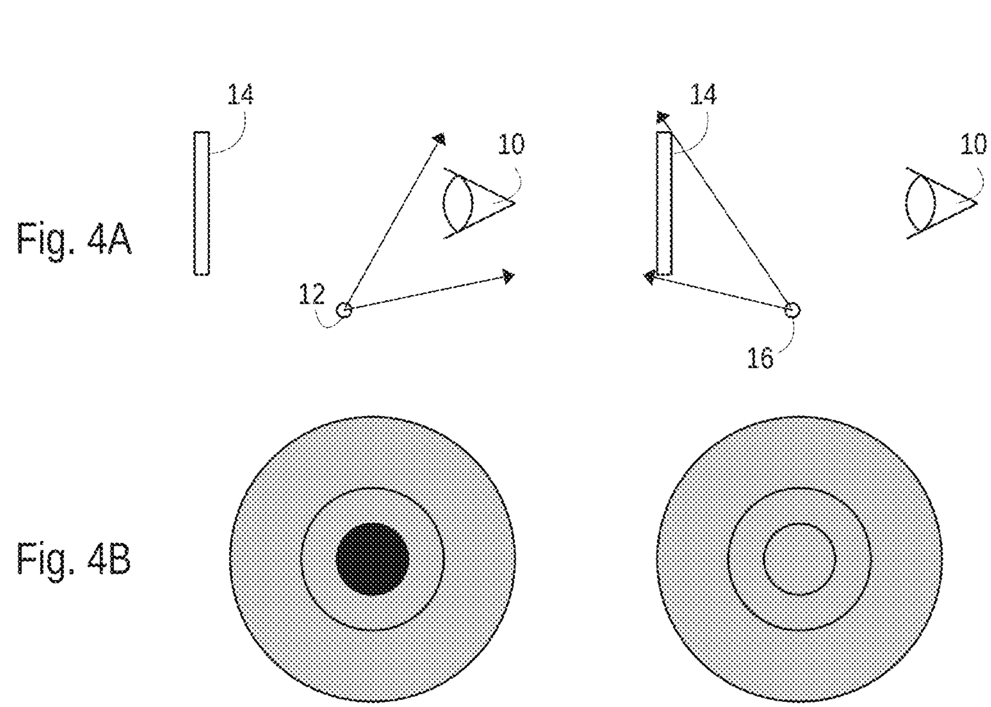
Fig. 4A
14
10
12
14
10
16
Fig. 4B
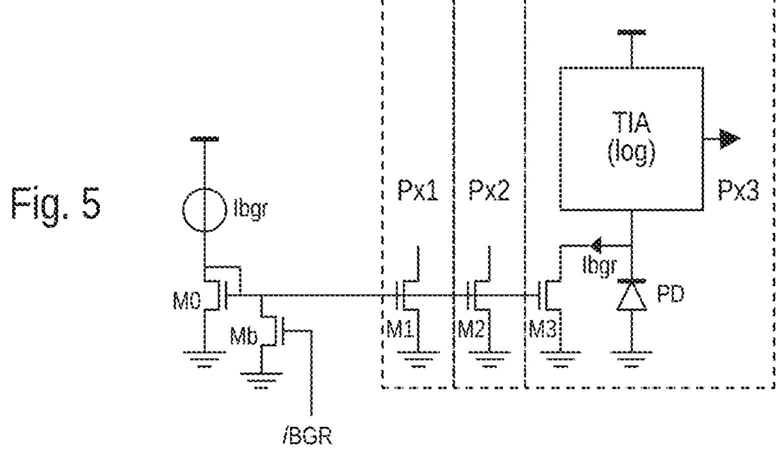
Fig. 5
Ibgr
M0
Mb
/BGR
Px1
Px2
Px3
M1
M2
M3
TIA
(log)
Ibgr
PD

PUPIL DETECTION USING AN EVENT-BASED SENSOR

CROSS-REFERENCE TO RELATED APPLICATION

This application is based on and claims priority under 35 U.S.C. 119 to European Patent Application No. 23315173.7 filed on May 9, 2023, the disclosure of which is herein incorporated by reference in its entirety.

TECHNICAL FIELD

The present disclosure relates generally to eye-tracking techniques using pupil detection methods.

BACKGROUND

Eye-tracking may be implemented in various devices such as virtual or augmented reality glasses or goggles, camera viewfinders, etc. Eye-tracking is often based on pupil detection with vision sensors and specific illumination conditions, usually with infrared sources that do not disturb the normal vision.

A "bright pupil" detection technique generally involves illuminating the retina through the pupil with a source placed near the optical axis of the camera, or sufficiently far in front of the eye that it appears to be on the optical axis. Under such conditions, the pupil appears to be very bright relative to its surroundings and is relatively easy to detect through contrast differences. Such techniques are not suited to devices placed close to the eye (goggles, glasses, viewfinders), since the infrared source cannot be placed close enough to the optical axis with respect to its distance to the pupil.

A "dark pupil" detection technique is better suited to devices close to the eye. It involves illuminating the eye from the side, whereby the pupil absorbs almost all light and appears much darker than its surroundings.

Detection is usually carried out with a frame-based camera and an image analysis performed on the frames produced by the camera. To save power, the eye is illuminated intermittently or flashed at the rate of the frames. The technique however remains power-hungry, because it involves performing an analysis on a significant amount of frame data. Moreover, frame-based sensors cannot detect movements faster than the frame rate, and increasing the frame rate to capture faster movements would increase the required computation power.

The use of event-based sensors in pupil detection applications overcomes the lack of speed of frame-based sensors, but the amount of data to process remains large, as shown below.

FIGS. 1A and 1B illustrate two phases of a dark pupil detection method conventionally using an event-based sensor and an intermittent illumination of the eye. Since there is no frame rate limitation, the illumination flash frequency may approach the reaction speed limit of the event-based sensor.

FIG. 1A illustrates the appearance of the eye as perceived by the sensor in the two illumination phases, and FIG. 1B illustrates a corresponding brightness variation of the pupil and the rest of the eye. On the left, there is no illumination, and the eye and pupil are uniformly dark (black). On the right, the illumination is turned on. The pupil remains dark or is barely brighter, whereas the rest of the eye becomes significantly brighter (white).

It is thus apparent that a large number of pixels around the pupil, in any case more pixels than in the pupil area, see a significant contrast change. As a consequence, an event-based sensor will trigger a significant number of events that require a corresponding amount of processing power. In essence, although the use of an event-based sensor for dark pupil detection improves the speed of detection, the amount of processing power remains significant.

SUMMARY

A general method is provided for detecting a pupil of an eye with an event-based vision sensor, comprising the steps of directing a first light source towards the eye; observing the eye with the event-based sensor; and intermittently submitting the sensor to a uniform background signal.

The method may further comprise the steps of setting a level of the background signal such that a relative brightness change sensed for the pupil is greater than a relative brightness change sensed for the rest of the eye; and setting a detection threshold of pixels of the sensor such that the relative brightness change of the pupil triggers an event, and the relative brightness change of the rest of the eye does not trigger an event.

The method may further comprise a step of submitting the sensor to the background signal during phases where the eye is illuminated with the first light source.

The method may alternatively comprise a step of illuminating the eye in phase opposition with the background signal.

The background signal may be increased gradually until events are triggered by the sensor.

The background signal may be obtained by directing a second light source towards the sensor.

The background signal may alternatively be an electrical signal added inside pixel circuits of the sensor that has the effect of a uniform illumination of the sensor.

The electrical signal may be a constant current added to photocurrents generated in the pixels.

The sensor may be fitted with a lens, and the second light source may be arranged such that light partially reflected by the lens penetrates a pupil of the eye.

The first light source may be a display device viewed by the eye.

A general method is also provided for detecting a pupil of an eye with a vision sensor fitted with a lens, comprising the steps of observing the eye with the sensor; directing a light source towards the lens of the sensor such that i) the sensor is submitted to a uniform background signal and ii) light partially reflected by the lens penetrates a pupil of the eye; and performing a bright pupil detection on the image perceived by the sensor.

BRIEF DESCRIPTION OF THE FIGURES

Embodiments will be exposed in the following description provided for exemplary purposes only, in relation to the appended drawings, in which:

FIGS. 3A and 3B illustrate absolute and relative logarithmic contrast variation graphs used in the embodiment of FIGS. 2A-2C;

FIGS. 4A and 4B illustrate two phases of a dark pupil detection method using an event-based sensor according to a second embodiment; and FIG. 5 illustrates partial pixel circuits modified according to an embodiment to add a uniform background signal.

DETAILED DESCRIPTION OF THE EMBODIMENTS

Figures 1A, 1B, 2A, 2B, 2C:
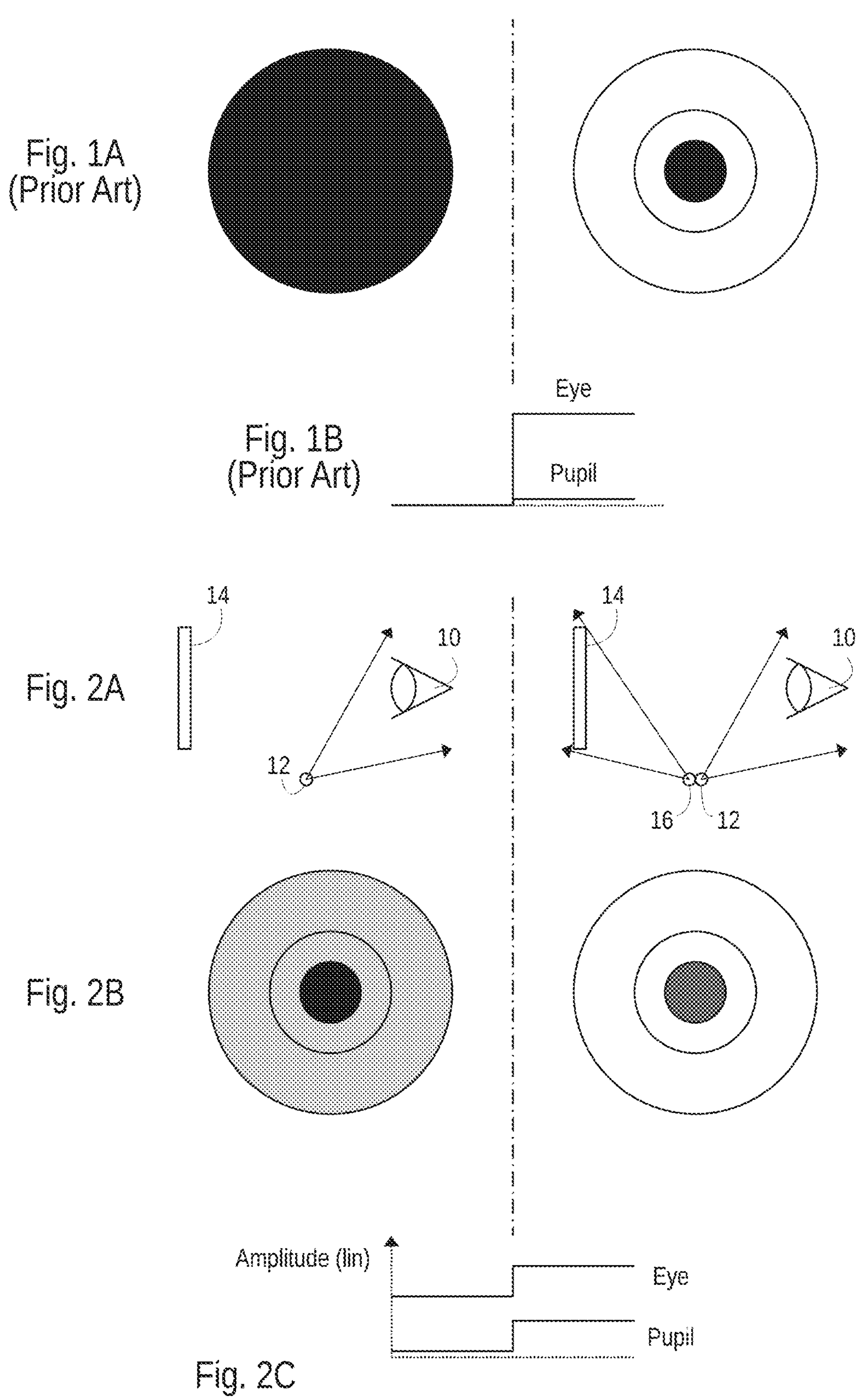
FIGS. 1A and 1B illustrate two phases of a dark pupil detection method conventionally using an event-based sensor and an intermittent illumination of the eye.
FIGS. 2A-2C illustrate two phases of a dark pupil detection method using an event-based sensor according to a first embodiment.

As previously mentioned, when performing eye tracking with an event-based sensor using a dark pupil method and intermittent illumination of the eye, the number of events triggered at each illumination flash, i.e., the amount of data to process, is significant. This is because a significant portion of the eye sees a brightness change that triggers events, whereas the region of interest, the pupil, sees hardly any change and triggers no events.

It is proposed herein to illuminate the eye under specific conditions that reverse the regions that see a significant brightness change, i.e., such that the pupil sees the most significant change, whereas the rest of the eye sees a change insufficient to trigger events.

FIGS. 2A-2C illustrate, respectively, a first embodiment of a two-phase illumination configuration, a corresponding eye appearance variation as perceived by the sensor, and a corresponding brightness variation of the eye and pupil regions.

In a first phase, on the left, the eye 10 is illuminated by a source 12, preferably infrared, placed, for instance, between the eye and the sensor 14, and offset with respect to an optical axis between the eye and the sensor, in a dark pupil configuration. The sensor includes an array of event-based pixels and is usually fitted with a lens, not shown. Both the sensor and the source 12 may be located on a rim of glasses or goggles worn by the user. In other configurations, the source 12 may be located in a plane behind the sensor and may even be the display device usually included in goggles.

The illumination intensity of the source 12 need not be as bright as required in a conventional situation. As shown on the left of FIG. 2B, the pupil remains dark, and the surrounding region is gray instead of white. Exemplary brightness levels are shown on the left of FIG. 2C, on a linear amplitude scale—the pupil brightness is barely above zero, whereas the rest of the eye region has a brightness at a given level, shown as lower than that of the conventional illumination phase of FIG. 1B, as an example, to save power.

In a second illumination phase, on the right, the sensor 14 is submitted to a uniform background signal. This background signal may be produced, as shown as an example, by a second illumination source 16 directed towards the sensor. The source 16 may be placed outside a sensor housing incorporating the lens and be directed towards the lens. The source 16 could also be placed inside the sensor housing and could thus be in the visible spectrum since it wouldn't interfere with the user's vision. Alternatively, the background signal may be an electrical signal added inside the pixel circuits that would produce the same effect as a uniform illumination of the sensor, for example a constant bias current added to the photocurrent of each pixel in the sensor array, as described below in relation to FIG. 5.

This background signal causes all regions viewed by the sensor to see their brightness increase by a same step, as illustrated on the right of FIG. 2C. As shown on the right of FIG. 2B, for purposes of illustration, the pupil changes from black to gray, whereas the rest of the eye changes from light gray to white.

This mechanism finds its relevance in the way the event-based pixels are generally designed, i.e., brightness is measured on a logarithmic scale and changes on such a logarithmic scale correspond to ratios of change. The ratio of brightness change for the pupil happens to be much larger than the ratio of brightness change for the rest of the eye with the shown illumination method.

FIG. 3A shows the brightness evolutions of FIG. 2C on a logarithmic amplitude scale. Here, the step seen by the pupil is significantly larger than the step seen by the rest of the eye, because the brightness of the pupil increases from nearly zero, whereas the brightness of the rest of the eye increases between two values that are relatively far from zero.

FIG. 3B illustrates comparisons carried out by event-based pixels corresponding to the pupil region and the rest of the eye region. Each pixel is usually designed to compare the logarithmic amplitude changes to a threshold, i.e., the difference between the current logarithmic amplitude and the previous logarithmic amplitude, which reflects the ratio of change. The threshold Th may be set, as shown, such that the change for the pupil region exceeds the threshold, whereas the change for the rest of the eye region stays below the threshold. This configuration provides a certain latitude for the choice of the intensities of the sources 12 and 16 to lower the power consumption.

In one example, the source 12 illuminating the eye may be on continuously, but its intensity may be significantly less than required in the conventional setup of FIGS. 1A, 1B. The intensity of intermittent source 16 may also be set at a relatively low level.

Alternatively, the two shown illumination phases may be interleaved with stand-by phases where both sources are off and the sensor is disabled.

To optimize power consumption, the intensity of the background illumination source 16 may be increased gradually instead of in a single large step, until events that correspond to the pupil region are triggered.

FIGS. 4A and 4B illustrate two phases of a dark pupil detection method using an event-based sensor according to a second embodiment. In FIG. 4A, a layout similar to that of FIG. 2A is used for the sensor and illumination sources. However, instead of continuously illuminating the eye with source 12 and flashing source 16 to intermittently add the background illumination signal, sources 12 and 16 are flashed in phase opposition. On the left side, source 12 illuminates the eye while source 16 is off, creating an image similar to that on the left of FIG. 2B, revealing a dark pupil and a brighter surrounding region, shown as gray. On the right side, source 16 illuminates the sensor while source 12 is off, creating an image having a uniform brightness level shown as gray.

In theory, the brightness levels of the rest of the eye region in both phases could be made substantially equal by adjusting the intensities of the sources 12, 16, whereby no difference would be measurable for this region, thus increasing the discrimination tolerance for detecting the pupil. This may however be difficult in practice, since the two phases correspond to different illumination conditions (the eye on one side and the sensor on the other side). In any case, like for the embodiment of FIGS. 2A-2C, the ratio of change for the pupil region remains substantially larger than the ratio of change for the rest of the eye region.

FIG. 5 illustrates pixel circuits of an array modified according to an embodiment to add a uniform background signal within the sensor array. Three pixels Px1-Px3 are partially illustrated, where pixel Px3 is illustrated in more detail. Each pixel of an event-based sensor generally includes a photodiode PD having its anode connected to ground. The photocurrent generated by the diode flows from a high supply line into the cathode of the photodiode through a transimpedance amplifier TIA that usually has a logarithmic response. The output of the TIA is processed by circuitry, not shown, to produce events in any known manner.

A respective N-MOS transistor M1-M3 is connected between the cathode of each photodiode and ground. The transistors M1-M3 form outputs of current mirrors sharing a common diode-connected input N-MOS transistor M0. A current source Ibgr is connected to inject a background reference current Ibgr in the diode-connected transistor M0, which current is copied in each of transistors M1-M3 and adds to the photocurrent measured by the TIA. The current Ibgr is adjusted to produce the desired background signal intensity.

An N-MOS transistor Mb connects the gates of transistors M0-M3 to ground and is controlled by an active-low background enable signal/BGR. Signal/BGR may thus switch the sensor between a normal mode and a simulated background illuminated mode.

As previously mentioned, one embodiment of the background signal source 16 is an illumination source directed towards a lens of the sensor, according to the configuration shown at the right of FIG. 2A. The lens will partially reflect the light of source 16 along a cone. If the source 16 is sufficiently close to the optical axis or the lens has a sufficient curvature, the reflected cone may intersect the pupil, whereby light penetrates the pupil along the optical axis, putting the pupil in bright pupil detection conditions.

Such a configuration further increases the brightness variation of the pupil. In other words, the linear amplitude step for the pupil in FIG. 2C is greater than the step for the rest of the eye. As an illustration, at the right of FIGS. 2B and 4B, where the source 16 is turned on, the pupil will be a lighter shade of gray.

This particular configuration may be simplified, by using only the source 16, to operate a bright pupil detection technique. The source 16 is then permanently turned on at a relatively low intensity, generating a uniform gray background on the sensor. The source 12 is absent or permanently off. The light partially reflected by the lens illuminates the eye and pupil, which create an image with a bright pupil superimposed on the background gray level of the sensor. The pupil region, although it may not be as bright as in the situation of an appropriately exposed eye, will still be noticeably brighter than the rest of the perceived image. The pupil will thus be relatively easy to track with any type of sensor (event-based or frame-based), offering the advantage of bright pupil sensing techniques, i.e., avoiding the false positives a dark iris may cause with dark pupil sensing techniques.

What is claimed is:

1. A method for detecting a pupil of an eye with an event-based vision sensor, the method comprising the steps of:

directing a first light source towards the eye;

observing the eye with the event-based vision sensor; and intermittently submitting the event-based vision sensor to a uniform background signal that is applied to the event-based vision sensor independently of light reflected from the eye, the uniform background signal causing all regions viewed by the event-based vision sensor to see their brightness increase by a same step.

2. The method of claim 1, comprising the steps of:

setting a level of the background signal such that a relative brightness change sensed for the pupil is greater than a relative brightness change sensed for the rest of the eye; and setting a detection threshold of pixels of the event-based vision sensor such that the relative brightness change of the pupil triggers an event, and the relative brightness change of the rest of the eye does not trigger an event.

3. The method of claim 2, comprising a step of submitting the event-based vision sensor to the background signal during phases where the eye is illuminated with the first light source.

4. The method of claim 2, comprising a step of illuminating the eye in phase opposition with the background signal.

5. The method of claim 1, wherein the background signal is increased gradually until events are triggered by the event-based vision sensor.

6. The method of claim 1, wherein the background signal is obtained by directing a second light source towards the event-based vision sensor.

7. The method of claim 1, wherein the background signal is an electrical signal added inside pixel circuits of the event-based vision sensor that has the effect of a uniform illumination of the event-based vision sensor.

8. The method of claim 7, wherein the electrical signal is a constant current added to photocurrents generated in the pixel circuits.

9. The method of claim 6, wherein the event-based vision sensor is fitted with a lens, and the second light source is arranged such that light partially reflected by the lens penetrates a pupil of the eye.

10. The method of claim 1, wherein the first light source is a display device viewed by the eye.

11. A method for detecting a pupil of an eye with a vision sensor fitted with a lens, the method comprising the steps of:

observing the eye with the vision sensor;

directing a light source towards the lens of the vision sensor such that i) light from the light source that reaches the vision sensor through the lens submits the vision sensor to a uniform background signal and ii) light reflected by the lens towards the eye penetrates a pupil of the eye; and performing a bright pupil detection on an image perceived by the sensor, the pupil appearing brighter than surrounding regions of the eye in the image due to the light reflected by the lens.

* * * * *